US 6,730,223 B1

(12) United States Patent
Anderson et al.

(10) Patent No.: US 6,730,223 B1
(45) Date of Patent: May 4, 2004

(54) APPARATUS, SYSTEM AND METHOD FOR TREATING WASTE MATERIAL

(75) Inventors: Joseph Anderson, Reno, NV (US); David Vincent Bozzi, San Francisco, CA (US)

(73) Assignee: Comprehensive Resources, Recovery & Reuse, Inc., Reno, NV (US)

( * ) Notice: Subject to any disclaimer, the term of this patent is extended or adjusted under 35 U.S.C. 154(b) by 0 days.

(21) Appl. No.: 10/285,471

(22) Filed: Nov. 1, 2002

(51) Int. Cl.$^7$ ................................................. C02F 3/28
(52) U.S. Cl. .................. 210/603; 210/612; 210/615; 210/181; 210/194; 210/259
(58) Field of Search .................. 210/603, 612, 210/615–617, 175, 181, 194, 259, 173

(56) References Cited

U.S. PATENT DOCUMENTS

| | | | |
|---|---|---|---|
| 3,010,581 A | * 11/1961 | Knapp et al. | 210/151 |
| 4,997,568 A | * 3/1991 | Vandervelde et al. | 210/603 |
| 5,445,329 A | 8/1995 | Anderson | |
| 5,655,718 A | 8/1997 | Anderson | |
| 6,007,719 A | * 12/1999 | Yoo et al. | 210/603 |
| 6,024,876 A | * 2/2000 | Pannier et al. | 210/616 |

FOREIGN PATENT DOCUMENTS

DE 4415017 * 11/1995

* cited by examiner

Primary Examiner—Fred G. Prince
(74) Attorney, Agent, or Firm—Burns Doane Swecker & Mathis, LLP (57) ABSTRACT

A method, apparatus and system for processing municipal waste starts with a biomass that has been treated in at least one steam autoclave and dilutes the resulting biomass in a dilution tank while agitating the resulting mixture a sufficient amount and at an effective temperature to cause cellulose fibers within the biomass that became twisted during processing within the autoclave to relax and straighten out. The biomass mixture is fed into a hybrid anaerobic digester having separate zones for digesting the solid portion of the biomass and the fluid portion of the biomass. The hybrid anaerobic digester is a vessel having an inner zone for digestion of the solid portion of the biomass and a concentric outer zone having attached growth media that retains methane producing organisms which produce biogas from the fluid portion of the biomass.

30 Claims, 6 Drawing Sheets

APPARATUS, SYSTEM AND METHOD FOR TREATING WASTE MATERIAL

FIELD OF THE INVENTION

The present invention relates generally to the treatment of process materials such as municipal waste material. More particularly, the present invention pertains to an apparatus, system and method for treating process materials that have already been subjected to preliminary processing in a steam autoclave.

BACKGROUND OF THE INVENTION

Landfills are commonly used to dispose of waste materials of many different types. These waste materials can include paper products, food scraps, yard waste, metal, glass, plastic and a host of other materials. In an attempt to reduce the amount of waste material that is deposited in landfills, source separating efforts in the form of recycling programs have been instituted. To the extent they are used, such recycling programs help reduce landfill dependence. However, it has been found that such recycling programs only result in the removal of a relatively small percentage of the total waste material. In the case of at least some material, such as paper products and other materials, the relatively small recovery rate can be attributed at least in part to the fact that a large percentage of the products are food-contaminated and thus quite difficult to separate and recycle.

In commonly assigned U.S. Patent Nos. 5,445,329 and 5,655,718, which are incorporated herein by reference, the disclosed apparatus, system and methods for treating processed materials are well suited for effectively and efficiently treating materials of many different types, including municipal solid waste. Organic and inorganic materials can be conditioned by varying treatment parameters, thereby facilitating sorting by size and density separation into their primary components. The subject matter disclosed in the above-referenced patents allows separation of food waste, ink, oil, grease and other related products from a host of base materials, such as metal, glass and paper. Food products, for example, can be solubilized and then extracted from the waste stream. Additionally, a relatively clean, high quality form of cellulose can be recovered from the waste stream. It is also possible to obtain clean metal products, which are much more readily acceptable as feedstock for various industries. Likewise, paper products can be treated to produce high quality recyclable material that can be separated for use in various industries. For example, through use of a fractionator, longer fibrous material can be divided out from the shorter fibrous material, with the former having possible use in the paper industry as recycled paper, and the latter being converted to a fuel, possibly for use in the electrical industry.

The methods, apparatus and system disclosed in the above-referenced patents use heat and pressure combined with moisture variation and controlled venting and tumbling in order to refine the quality of the resulting feedstocks that are produced from the municipal waste. Heat is added to the steam autoclaves disclosed in the above-referenced patents both by the addition of steam directly into contact with the waste materials within the autoclaves, as well as by the introduction of a heated fluid which is transported through the interior of the vessels within conduits in order to heat and/or dry the material located in the steam autoclaves. The heat and pressure within the steam autoclaves is increased such that the steam reaches a saturated state, and then after a predetermined time, the steam is rapidly vented in order to drop the pressure within the vessels quickly from a higher pressure to a negative pressure, thus reaching a superheated state and causing a release of enthalpy from the conditioned waste materials within the vessels. The biomass that results from the processes disclosed in the above-referenced patents can then be passed through screens, with the screened waste material from the steam autoclaves constituting approximately 70% of the total incoming waste stream when the screens are provided with approximately ½ inch openings. This fraction of the total incoming waste stream also includes approximately 95% of all the organic materials present in the municipal waste.

SUMMARY OF THE INVENTION

The present invention provides an apparatus, system and methods for treating the separated biomass that results from processing within the steam autoclaves disclosed in the above-referenced patents, although the invention also has useful application for treating materials resulting from different processing. The present invention further enhances the qualities of the separated biomass produced by the above-referenced steam autoclaves in order to optimize its use as a feedstock for a number of recycling and secondary industries. The end product produced by the methods, apparatus and system according to the present invention includes cellulose fibers that are readily recyclable for the paper industry, and/or useful for cellulosic insulation, a residual fine fiber fraction that can be used in compost as a soil amendment or used directly as a solid fuel, and biogas that is also useful as a fuel.

The present invention works synergistically with biomass produced by the methods and systems disclosed in the above-referenced patents as a result of the enhancements to the biomass for use by the recycling industry. Some of the significant enhancements to the biomass produced by the methods and systems according to the above-referenced patents are enhancements to the organic material that result from the pressurized cooking and solubilization of the organic materials that occurs within the steam autoclaves. The food wastes and other organic materials processed through the steam autoclave are largely solubilized and have an increased biodegradability when compared to fibers that have not been processed through the steam autoclave. The tumbling action of the steam autoclaves also results in finer particles than would result after an expenditure of the same amount of energy in a conventional hydro-pulping process currently used to pulp waste paper. Other enhancements to the biomass produced by the steam autoclaves include the dispersion of oils, suspension of lacquers and inks, solubilizing of coatings, and after some successive gravity and density separations and size screenings as well as dilution rinsing, the production of a clean ligno-cellulosic fiber that is very low in debris and suitable for incorporation within secondary fiber pulp used for paper manufacturing.

The cellulose fibers that are separated from the biomass produced by the steam autoclaves have also been shown to have a significantly higher freeness, or ability to rapidly drain water, when compared to conventional sources of fiber such as recycled old corrugated containers and ground wood fiber. The higher freeness as well as improved strength characteristics of the fibers separated by methods and apparatus according to the present invention significantly increases the value of these processed cellulose fibers to the paper making industry since energy requirements are reduced with the paper making machines being able to run faster.

The temperatures of between 260° F. and 270° F. that are reached within the steam autoclaves also have been found to enhance the characteristics of the cellulose fibers separated from the biomass produced by the autoclaves. Paper fiber generally includes lignin that binds to the cellulose fiber, hemicellulose, which is the soluble portion of the cellulose, and cellulose, which is basically very difficult to solubilize unless it is treated with acids, etc. Because the softening point of the lignin is approximately 262° F., the temperatures reached within the steam autoclaves cause the lignin that binds to the cellulose fibers to be softened, but the lignin is not heated enough to be crystallized. Low melt point plastics within the biomass form into small beads that are easily separated during subsequent density and size separations so as to not be included with the cellulose fibers used by the paper industry.

In a method of treating waste material according to an embodiment of the invention, the waste material has first been subjected to increased temperature, pressure and mechanical shearing action in a steam autoclave to produce a biomass having at least one characteristic selected from a group of characteristics that are desirable in the recycling industries that use the various separated portions of the biomass. The enhanced characteristics of the separated portions of the biomass include the higher freeness or ability to rapidly drain water of the cellulose fibers that are provided to the paper recycling industry, good strength characteristics when compared to recycled corrugated cardboard containers and ground wood pulp, finer particle sizes than those that are achieved by conventional hydro-pulping of waste material for the same amount of energy consumed, aseptic properties, which result from the materials within the steam autoclave having been raised to high temperatures and pressures and then rapidly dropped to a negative pressure, the majority of the organic materials in the biomass being solubilized and the increased biodegradability of the cellulose fibers when compared to fibers that have not been autoclaved.

In a method, apparatus and system according to an embodiment of the present invention, the biomass having these enhanced characteristics can be subjected to separation processes wherein components of the biomass are separated by density, and/or size separation processes such as screening, wherein components are separated by size. A method according to an embodiment of the invention may also include the step of diluting the biomass with process water and subjecting the diluted mixture to a gentle mixing action, with the selected temperature and mixing action being effective to relax and straighten the cellulose fibers that have become twisted and tangled during the steam autoclave process. This latency removal step is used when the resulting cellulose fibers are to be further processed for use by the recycled paper industry.

In a method according to another embodiment of the invention, the biomass obtained from the steam autoclaves can be added to a sump or reservoir along with fluids obtained from a hybrid anaerobic digester that includes separate zones for biologically processing solids and fluids, to produce a solution with the proper ratio of solids to fluids for pumping and introduction to a gravity separation process such as in a liquid cyclone. The hybrid anaerobic digester allows for independent processing of solids and fluids, and therefore can provide all of the necessary fluids for operation of the liquid cyclone, thus working in an essentially closed loop with the liquid cyclone.

Additional processing of the biomass material and/or fine fiber fraction according to the invention can occur within a hybrid anaerobic digester, which is a vessel having separate zones for the biological processing of solid materials and fluid materials, with the processing of the fluid materials being independent from the processing of the solid materials. The vessel forming the hybrid anaerobic digester is preferably cylindrical with a conical bottom. The vessel has an outer wall that is cylindrically shaped over a portion of the height of the vessel, and conically shaped at the bottom portion of the vessel. A cylindrical intermediate wall is spaced inwardly from the outer wall, and a hydraulic reservoir is defined between the intermediate wall and the outer wall. An inner, cylindrical wall is spaced inwardly from the intermediate wall, with an attached growth media zone containing growth media defined between the inner wall and the intermediate wall. A lower portion of the inner wall is perforated to provide fluid communication between an inner zone defined within the inner wall and the attached growth media zone.

DETAILED DESCRIPTION

Figure 1:
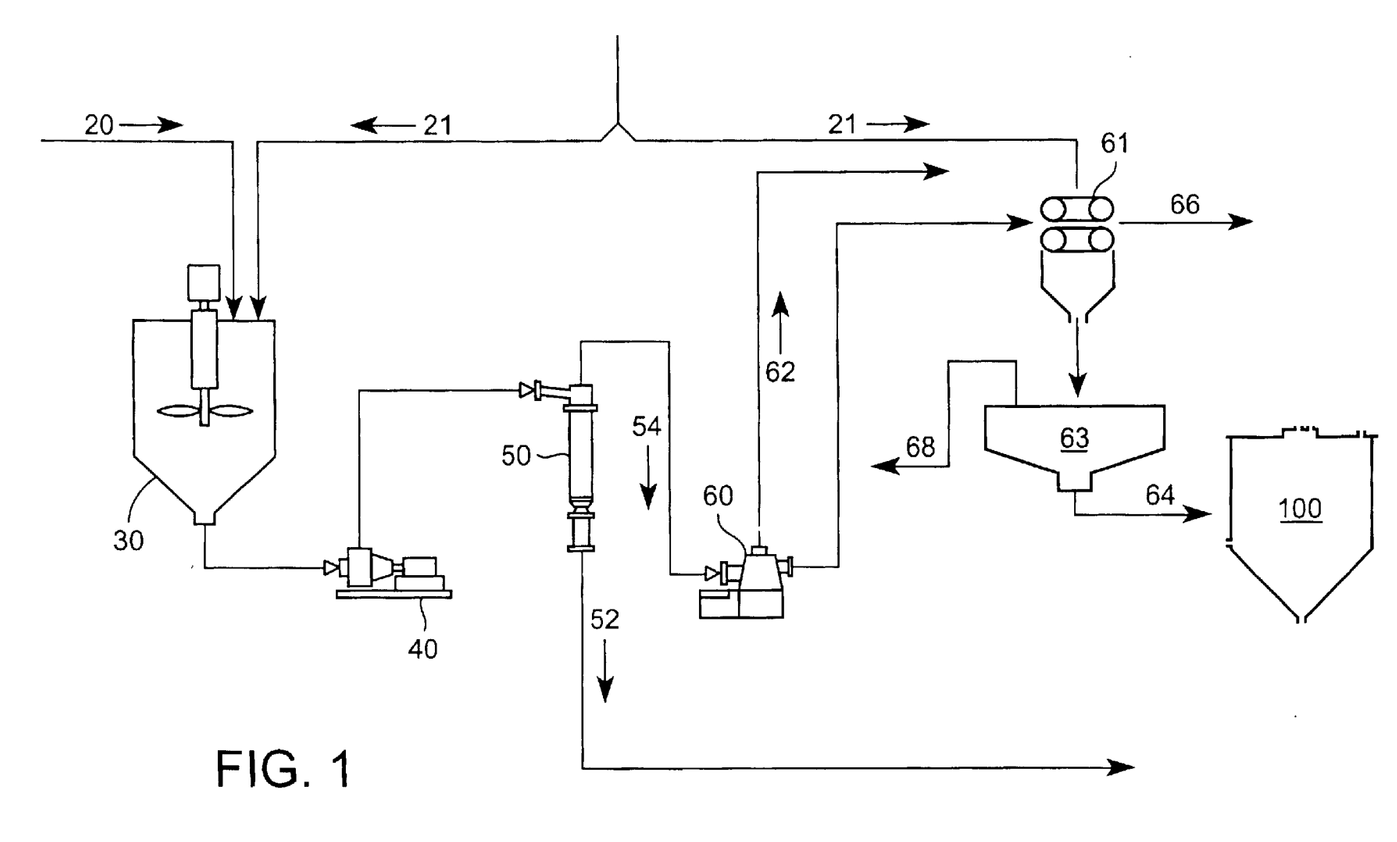
FIG. 1 is a schematic diagram illustrating a system and method for processing waste materials according to an embodiment of the invention.

With reference initially to FIG. 1, a system according to a preferred embodiment of the present invention includes various devices that are required for debris removal in the processing of a separated biomass obtained from a steam autoclave process such as described in detail in U.S. Patent Nos. 5,445,329 and 5,655,718, the disclosures of which are incorporated herein by reference. Although the invention has useful application to processing waste materials from a variety of sources, the following describes the invention in terms of processing a separated biomass resulting from the steam autoclave described in the aforementioned two patents. Municipal solid waste that was provided to the steam autoclave is generally made up of approximately 60% organic material and 40% inorganic material. Enhancements to the recyclable components of the biomass produced by the steam autoclaves work synergistically with the further processing performed according to embodiments of this invention.

After the steam autoclave process, approximately 95% of the 60% organic material from the municipal waste will pass through a half inch screen. The biomass that passes through the half inch screen typically represents approximately 65% by weight of the total amount of material that was originally put into the steam autoclave process. In addition to the 95% of the 60% organic material, the 65% of the total may include some glass and other debris. The 65% by weight of the total amount of municipal waste that was originally processed through the steam autoclave process carries almost all of the water, with the water including a large portion of solubilized organics. The 35% by weight of the total municipal waste that does not pass through a half inch screen after being processed in the steam autoclaves generally includes elements such as tin, plastics, glass and rags, which can be recycled using normal recycling methods.

The 65% by weight of the biomass that makes it through a half inch screen after coming out of the steam autoclave process is generally 50% water and 50% solids. The water includes the solubilized organics that can be divided into two main components. One of the solubilized components comes from waste, food and other starches, which have been solubilized as a result of the pressure cooking process that occurs in the steam autoclaves. The other main component of the organics is cellulose material, and the lignin that bonds to the cellulose. The cellulose portion of the organics generally originates from paper, and is also primarily carbohydrates, with the difference from the food starches being that the carbohydrates of most of the cellulose material are not readily solubilized and therefore remain as the solid portion of the biomass.

As shown in FIG. 1, in an embodiment where the cellulose material is processed for use by the paper recycling industry, the autoclaved biomass 20 (e.g., the biomass resulting from the operation of the steam autoclave described in the aforementioned patents) having approximately 50% solids consistency can be added to a dilution tank 30 with a sufficient amount of dilution water 21 in order to bring the consistency to approximately 4% solids and 96% water. The temperature in the dilution tank 30 is preferably kept around 130° F. while providing a gentle mixing action, which results in the relaxing and straightening (or latency removal) of cellulose fibers that became twisted and tangled during the steam autoclave process. The relaxing and straightening of the cellulose fibers that occurs as a result of diluting and mixing the biomass while maintaining the temperature around 130° F. in the dilution tank 30 has been found to improve the behavior of the cellulose fibers when they are used downstream in a recycled papermaking process.

After the diluting and relaxing or latency removal process that occurs in the dilution tank 30, the biomass then can be pumped by a pump 40 to a liquid cyclone 50 that performs a gravity separation process to separate the biomass by the density of its components. The liquid cyclone 50 spins out heavier material such as glass and grit 52, and allows these heavier, generally inorganic materials to be removed from the rest of the organic material. As a result of the density separation process that occurs in the liquid cyclone 50, a first portion 52 of the separated material includes the glass and grit debris having heavier density, and the remaining material 54 can be provided to a coarse pressure screen 60 for contaminant removal. The pressure screen 60 helps to separate out plastics and other floatable debris 62 that are not separated in the liquid cyclone 50.

After the density separation that occurs in the liquid cyclone 50 and the debris separation that occurs in the coarse pressure screen 60, approximately 98% of all of the debris has been removed. After separation of the plastics and floatable debris 62 from the screened biomass coming out of the coarse pressure screen 60, the remaining portion of the biomass can be subjected to further screening, pressing and diluting processes in order to separate or fractionate the cellulose fibers into longer fibers, which are useful to the paper industry, and shorter fibers, or fines, which can be fed to an anaerobic digester for the production of solid fuels or compost.

The longer cellulose fibers that are separated by coarse pressure screen 60 into the stream 66 shown in FIG. 1, are suitable for recycling by the paper industry and exhibit enhanced characteristics as a result of having been derived from the biomass 20 obtained from the steam autoclave apparatus and process described in the two patents mentioned above. The improved behavior of the biomass has been clearly demonstrated in a number of areas that relate to the reforming of the different types of organics uniquely caused by the steam treatment and the subsequent wet processing. One study that was carried out illustrated the improved freeness and strength characteristics in the production of market quality paper pulp. These enhanced characteristics in turn improve paper manufacturing by reducing energy requirements as they allow the paper machines to run faster, while reducing the total number of refining steps that are required. The temperature regimes used within the steam autoclaves are selected to approach the lignin melt point, which when combined with controlled multiple venting or rapid reduction in pressure after reaching saturated steam conditions, helps to produce the desirable enhancements for pulp recovery.

A second area in which treatability studies have verified the enhanced characteristics of the biomass resulting from the steam autoclave apparatus and process involves the improved biodegradability of the putrescible organics as they are solubilized. These improved characteristics were demonstrated in high rate anaerobic digesters where complete digestion of the solubilized organics was accomplished in very short time durations.

After removal of the longer fibers desirable to the paper industry, as represented by 66 in FIG. 1 by passing the stream through a beltpress device 61 for fractionating and rinsing the remaining cellulose fines, solids portion of the biomass 64 and fluids portion 68 are introduced to a clarifier device 63. The clarifier device 63 will allow for further separation by decanting the solids portion 64 and the fluids portion 68. The remaining solids portion of the biomass 64 can be provided to a hybrid anaerobic digester 100 according to an embodiment of the invention. The fluids portion 68 of the biomass separated out after the long fiber rinsing comprises the process water, which is now carrying solubilized organics and can be made available to a high rate anaerobic digester for anaerobic digestion to produce a biogas that is suitable for electrical cogeneration. The solids portion 64 of the biomass comprises primarily the short cellulose fibers or fines that are not amenable for recycling by the paper industry, and therefore are diverted to a high solids anaerobic digester, or more preferably, the hybrid anaerobic digester according to the invention, which produces both a biogas fuel as well as residual sludge suitable for compost and soil amendment.

Figure 3:
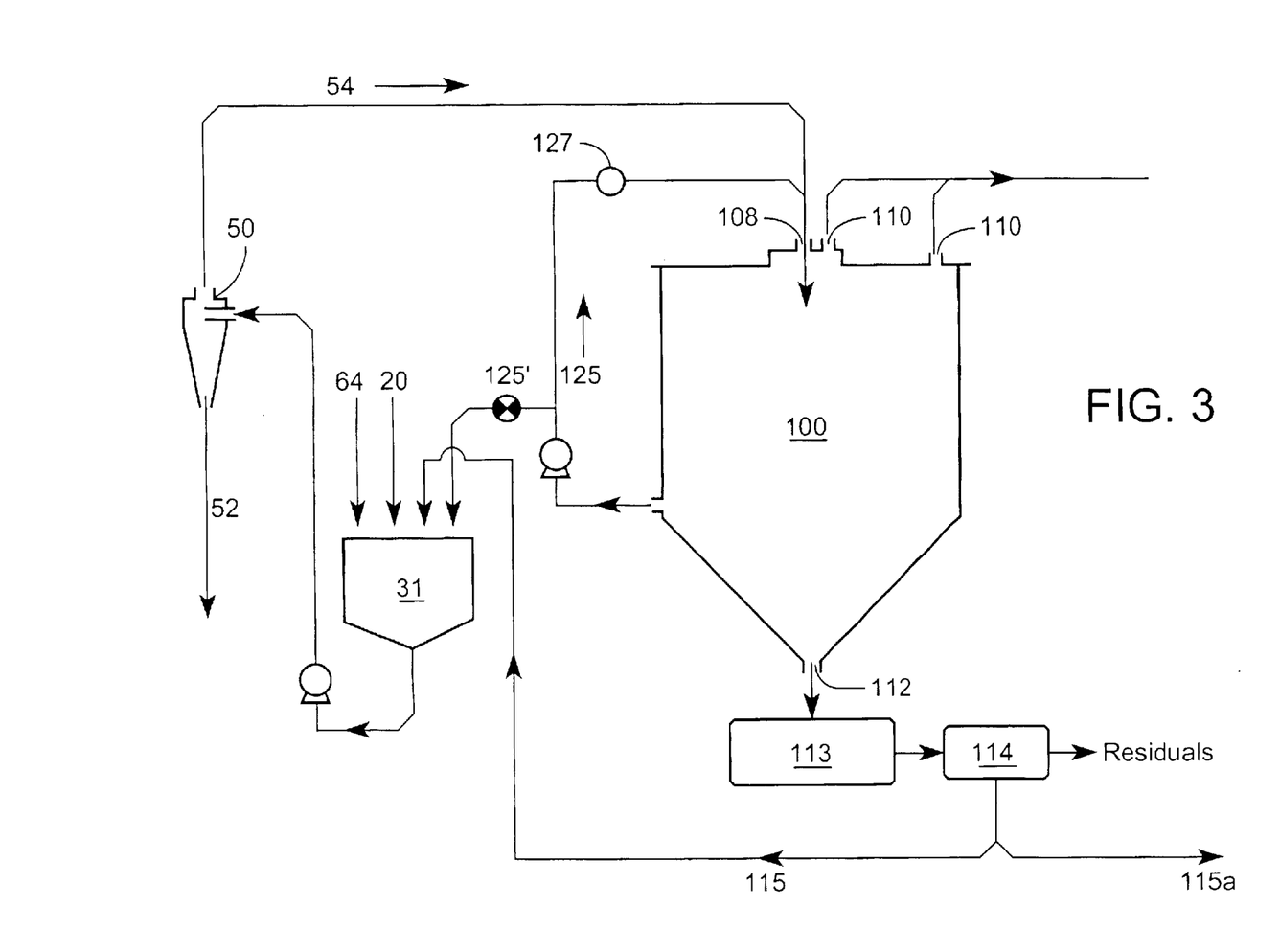
FIG. 3 is a schematic diagram illustrating a system and method for processing waste materials according to an embodiment of the invention.

In a further embodiment of the invention, as shown in FIG. 3, residual sludge can be pumped out of outlet 112 of a hybrid anaerobic digester 100 according to the invention using a high solids pump 113, and if desired can be subjected to a pressing operation in a press 114 to further separate any remaining fluids from the residual sludge. The pressate 115, 115a from press 114 can then be pumped to a sump or reservoir 31, or alternately routed for aerobic water treatment. Pressate 115 supplied to the sump 31 can be combined with autoclaved biomass 20, cellulose fines 64 and if desired a portion 125' of the fluids that are being recirculated from the hybrid anaerobic digester 100 for further processing within the hybrid anaerobic digester. This portion 125' can serve to innoculate the mix within the sump 31 with microorganisms that assist in the break down of the biomass, as well as providing the necessary amount of fluids to dilute the autoclaved biomass so that it can be pumped. The diluted mixture from sump 31 can then be subjected to further density separation in a liquid cyclone 50 and then reintroduced through inlet 108 to the hybrid anaerobic digester 100.

A certain portion of the cellulose fibers known as the fines, which are too short for paper making are separated and aggregated in a separate stream 64, as shown in FIG. 1. This stream can be directed into a high solids anaerobic digester, or more preferably provided to a hybrid anaerobic digester according to the invention, such as by introduction to the sump 31 in FIG. 3. The end products of the hybrid anaerobic digester include biogas that can be used for fuel and a high quality residual material suitable for compost or use as a soil amendment.

Figure 2:
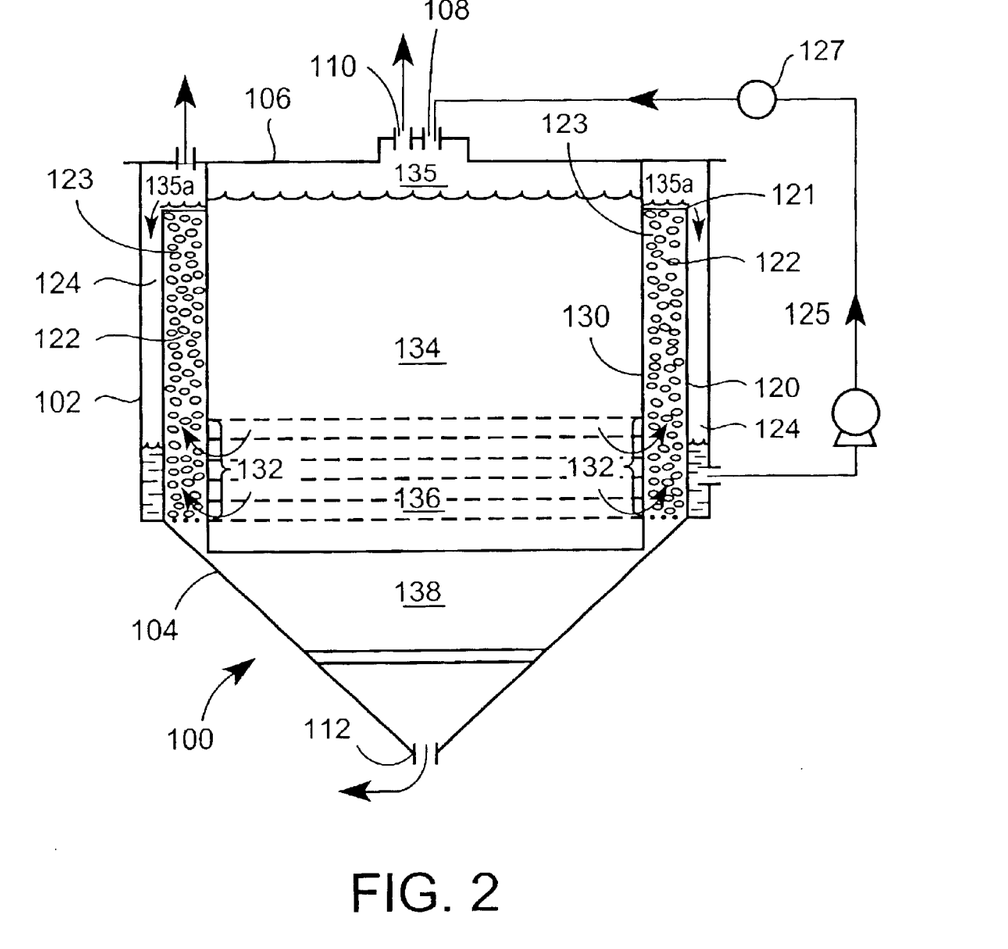
FIG. 2 illustrates a hybrid anaerobic digester according to an embodiment of the invention.

In accordance with a preferred embodiment of the invention, shown in FIG. 2, a hybrid anaerobic digester combines both a high solids anaerobic digester and a high rate anaerobic digester. The treated biomass 20 can be provided to the hybrid anaerobic digester 100 though inlet 108 after having been diluted and, if desired, subjected to a gravity separation process to remove debris, as shown in FIG. 3. The solids portion 64 of the treated biomass 20, comprising the fines that have been separated from the longer cellulose fibers to be used directly by the paper industry, can also be provided to the hybrid anaerobic digester 100 through inlet 108, in particular, after having been mixed with treated biomass 20 and subjected to a further gravity separation step if desired to remove debris.

The combined flow of the treated biomass and the short cellulose fibers or fiber fines is pumped into the hybrid anaerobic digester 100 through inlet 108, and the material is treated within the digester 100 in a temperature range of approximately 98° F. to 120° F., corresponding to the particular mesophilic and/or thermophilic biological cultures that are used within the various zones of the digester.

As shown in FIG. 2, the hybrid anaerobic digester 100 according to a preferred embodiment of the invention is a vessel having a substantially cylindrical outer wall 102 that tapers inwardly at a lower portion of the vessel to a conical bottom portion 104 having an opening 112 for removal of residual materials from the bottom of the vessel. An intermediate wall 120 is formed radially inward from and substantially concentric to the outer wall 102, and defines an annular hydraulic reservoir 124 between the intermediate wall 120 and the outer cylindrical wall 102. An inner wall 130 is formed radially inward from and substantially concentric to the intermediate wall 120, and an annular attached growth media zone 122 is formed between the inner wall 130 and the intermediate wall 120.

The vessel interior is divided into five primary zones. A biogas head space 135 is defined at the upper portion of at least the inner zone or high solids zone 134 defined within the inner wall 130. The high solids zone 134 defined within inner wall 130 receives the biomass material that is fed into the hybrid anaerobic digester through an inlet 108 at the top of the vessel 100. A leaching zone 136 is formed at the lower end of the high solids zone 134, and is defined on its outer perimeter by a perforated section 132 of the inner wall 130. Liquids from the high solids zone 134 pass through the perforations in section 132 of the inner wall 130 and enter the attached growth media zone 122 defined between inner wall 130 and intermediate wall 120. Solids from the high solids zone 134 fall down through bars that can be placed across the diameter of the vessel to assist in breaking up the solids as they pass into the conical compaction zone 138 defined by the lower conical portion 104 of the vessel 100.

A top edge 121 of the intermediate wall 120 defines a weir over which the liquids from within attached growth media zone 122 can flow into a hydraulic reservoir zone 124 defined between the intermediate wall 120 and the outer wall 102 of vessel 100. A recycling line 125 can tap off of the hydraulic reservoir 124 and recycle a portion of the liquids from the hydraulic reservoir back into the top of the high solids zone 134. The recycle loop 125 can include a heat exchanger 127 shown in FIGS. 2 and 3 in order to aid in the maintaining of a desired temperature within the vessel 100, which is critical to the growth of the microorganisms that break down the waste materials.

The selection of a particular attached growth media 123 provided in attached growth media zone 122 affects the volume of the attached growth media zone 122 that is necessary as a percentage of the total vessel volume in order to obtain the desired processing characteristics. A less expensive media, such as coarse rock, would require a higher attached growth media zone volume since the coarse rock provides a smaller total surface area per volume than would other, more expensive attached growth media. A cost/benefit analysis can determine whether a cheaper growth media should be used, requiring a larger tank size, or a more expensive growth media, enabling the use of a smaller tank size.

A head space 135, 135a remains above the high solids zone 134 and the attached growth media zone 122 and hydraulic reservoir 124. The head space 135 can be contiguous with head space 135a, or the two can be separated and provided with separate biogas outlets 110. Biogas produced by the anaerobic digestion of the solids in the high solids zone 134 and anaerobic digestion of the fluids in the attached growth media zone 122 collect in the head space 135, 135a and are removed from outlets 110 for use as fuel. The biogas is typically a mixture of carbon dioxide and methane, generally having between 60% and 65% methane, with the rest being carbon dioxide.

The liquid that is tapped off of hydraulic reservoir 124 through a recycle line 125 to be added back into the high solids zone through inlet 108 serves two purposes of re-inoculating the media by returning some of the microorganisms contained in the fluids, as well as providing for heat distribution. The heat exchanger 127 provided in the recycle line 125 aids in the maintenance of the temperature within the reactor in a desired range.

The solids from the high solids zone 134, along with any fluids that have not leached out through the perforations 132 into the attached growth media zone 122, drop down through breaker bars to enter into the compaction zone 138 within the lower conical section 104 of the reactor. The compaction zone is not active biologically and therefore does not have gas bubble formation that would tend to keep the solids from settling. It is a quiescent zone, so the residuals that are pumped out of the lower outlet 112 include debris such as glass, plastics, and unreacted cellulose fibers in a high concentration. The residuals that are pumped out of the lower outlet 112 can be subjected to further processing, such as shown in FIG. 3, including pressing, with the solids portion being further separated by size through screening to remove the glass, plastics and other debris, and then used directly as fuel or more specifically as a compost to form a soil amendment.

In a preferred embodiment of the invention, the solids within the high solids zone 134 have approximately a fifteen day cycle time from when the biomass is added into the top inlet 108 to when the residual material is pumped out of the lower outlet 112. Approximately 50% of the biomass that is added to the reactor vessel 100 through inlet 108 is digested by the microorganisms within the high solids anaerobic zone 134 and converted to a biogas containing methane and carbon dioxide, with the remaining 50% being the portion that is extracted from the outlet 112 to be used as a solid fuel or to be screened, further processed, and/or composted for an additional period.

The fluids containing solubilized organics pass from leaching zone 136 into the attached growth media zone 122. Because the fluids are kept separate from the solids within the hybrid anaerobic digester 100, the processing of the fluids and the solids can also be kept independent from each other. This arrangement provides significant advantages over conventional high solids digesters wherein the fluid portion of the biomass added to the high solids digester is intrinsically tied together with the processing of the solids. One of the advantages of the combined system according to an embodiment of the present invention results from the fact that the conversion of the solubilized organics in the fluid portion into biogas is much more efficient than the conversion of the solid organics within the high solids zone 134. In fact, nearly 100% of the solubilized organics within the fluid portion is digested, while only 50% of the solid portion is digested.

Another advantage of the arrangement for a hybrid anaerobic digester as shown in FIG. 2, is that a portion of the fluid from the hydraulic reservoir 124 can be recycled back into the high solids zone 134 and provide a means for re-innoculating the biomass within the high solids zone as well as controlling the temperature maintained within the vessel. The attached growth media contained in the attached growth media zone 122 as well as fluids in hydraulic growth media zone 124 make the vessel 100 essentially self-insulating. Furthermore, the recycle line 125 allows for the addition of heat to the portion of the fluid that is returned to the vessel.

Another significant advantage of the arrangement for a hybrid anaerobic digester having the separate high solids zone and hydraulic or fluid zones, as shown in FIGS. 2 and 4A–4F, is that the amount of time the fluids are retained within the vessel can be controlled independently from the amount of time that the solids are retained within the vessel. The fluid portion of the biomass that is added to the vessel through inlet 108 is leached from the solids within high solids zone 134, and passes from the leaching zone 136 through perforations 132 in inner wall 130 into the attached growth media zone 122.

Within attached growth media zone 122, the fluid containing solubilized organics continues to be digested by microorganisms attached to the media, as the solids from high solids zone 134 settle down into the compaction zone 138 and are removed from the outlet 112 of vessel 100. As a result, solids may be processed within the vessel, digested, and removed from the vessel within a relatively short period of time, such as a fifteen day cycle, while the fluids continue to be recirculated from the attached growth media zone 122 and hydraulic reservoir 124 back into the high solids zone 134. The separation of the amount of time that solids are retained within the vessel, commonly referred to as solid retention time (SRT), from the amount of time that fluids are retained within the vessel, commonly referred to as hydraulic retention time (HRT), gives much greater process flexibility for at least the reasons discussed below.

The organisms that are innoculated into the biomass introduced into the vessel 100 are generally a mixed culture media including a family of different organisms that perform different functions in the processing of the waste materials. As an example, during the processing of cellulose material by these microorganisms, the cellulose first has to be hydrolyzed, by a group of organisms referred to as acid formers. The acid forming organisms attack the carbohydrates in the cellulose and convert it into long chain volatile fatty acids. Then another group of organisms that are hydrogen reducing organisms work on the volatile fatty acids to strip off a hydrogen molecule and reduce the volatile fatty acids to an acetic acid. Finally, a group of organisms known as the methane formers, which are the slowest growing of all of the organisms, convert the acetic acid into carbon dioxide, methane and water.

Because the methane forming organisms are the slowest growing of all of the organisms, if the fluids within the biomass were removed with the solids after only a fifteen day cycle time or shorter, the methane forming organisms would be washed out of the vessel before they had a chance to reproduce. The hybrid anaerobic digester vessel 100 according to an embodiment of the present invention allows for a relatively low SRT, such as a twelve to fifteen day cycle time, while still retaining the slow growing methane producing organisms in the attached growth zone. The attached growth media zone 122 then acts like an organic capacitor as it retains the organisms that produce methane for a long enough time to allow the efficient production of biogas during the digestion process.

An example of a hybrid anaerobic digester according to one embodiment of the invention is shown in FIGS. 4A–4F, wherein the approximate dimensions of an embodiment of the vessel and the proportions of the total volume of the vessel assigned to each of the zones within the vessel are illustrated. It will be understood by one of ordinary skill in the art that the dimensions are not limiting in any way, and are merely representative of one embodiment of a hybrid reactor vessel that provides the advantages according to the present invention.

Figure 4A:
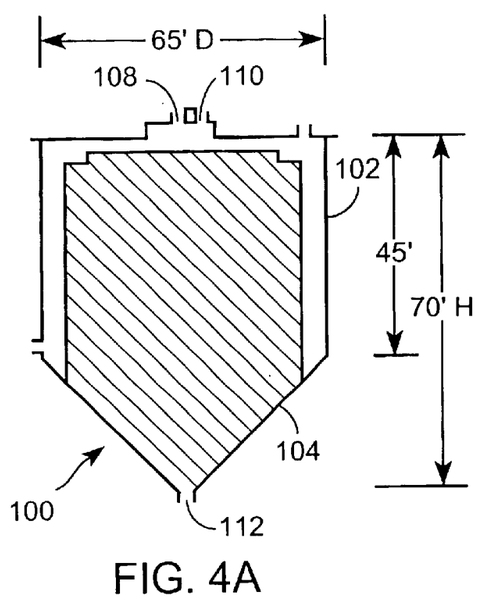
FIGS. 4A–4F illustrate an example of the relative volumes of various zones within a hybrid anaerobic digester according to an embodiment of the invention.
Figure 4B:
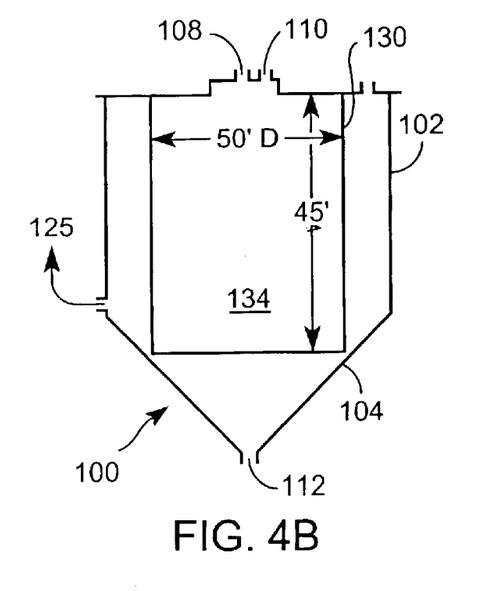
Figure 4C:
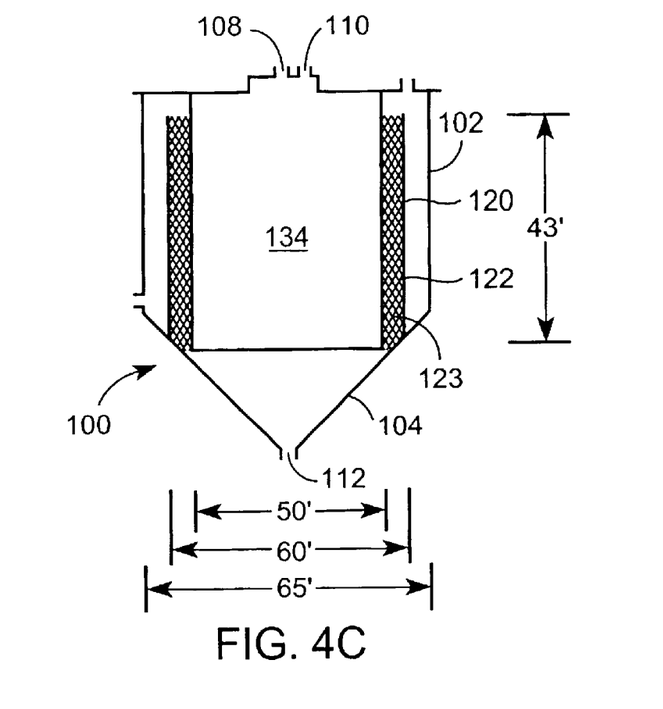

In the example shown in FIGS. 4A–4F, a hybrid anaerobic digester vessel is approximately 65 feet in diameter, and 70 feet high, with a conical lower portion that is approximately 25 feet high and a cylindrical upper portion that is approximately 45 feet high. The total reactor volume is approximately 188,034 cubic feet. The total hydraulic or fluids volume (which includes the volume of the high solids zone since the biomass added to the vessel is approximately 50% solids and 50% fluids, the volume of the attached growth media zone, and the volume of the conical compaction zone below the cylindrical high solids zone) is approximately 74% of the total reactor volume—or 138,617 cubic feet. For this particular example of a hybrid anaerobic digester according to an embodiment of the invention, the high solids zone, as shown in FIG. 4B, is approximately 50 feet in diameter and 45 feet high.

The attached growth media zone 122 will vary in volume depending on the particular type of growth media 123 that is chosen. A highly specialized growth media with a large surface area to volume ratio may only require that the volume of the attached growth media zone 122 is approximately 40% of the volume of the high solids zone 134. A lower cost media such as coarse rock, may require a volume of the attached growth media zone that is approximately 60% of the volume of the high solids zone. An attached growth media zone containing the highly specialized media will have approximately a 50 foot inner diameter and a 60 foot outer diameter in order to achieve a volume that is approximately 42% of the volume of the high solids zone.

Figure 4D:
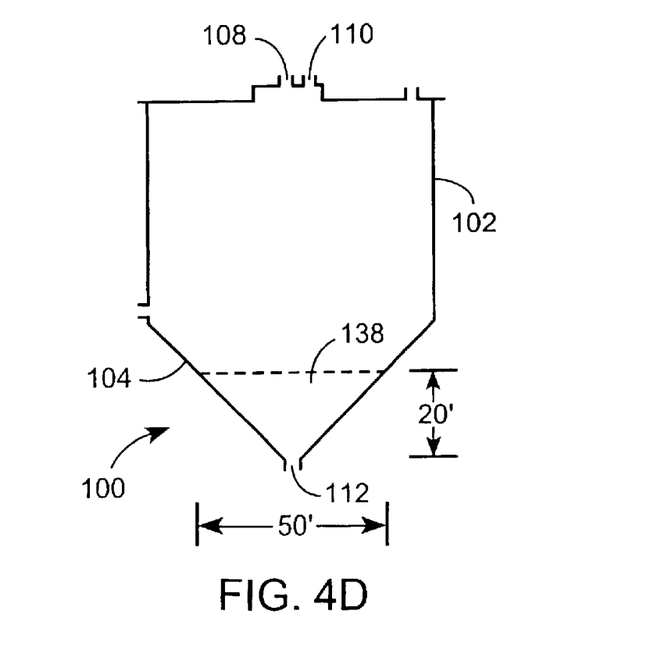

The compaction zone 138 in the example shown in FIG. 4D has a depth of approximately 20 feet in the lower conical portion 104 of the vessel, with a largest diameter of approximately 50 feet.

Figure 4E:
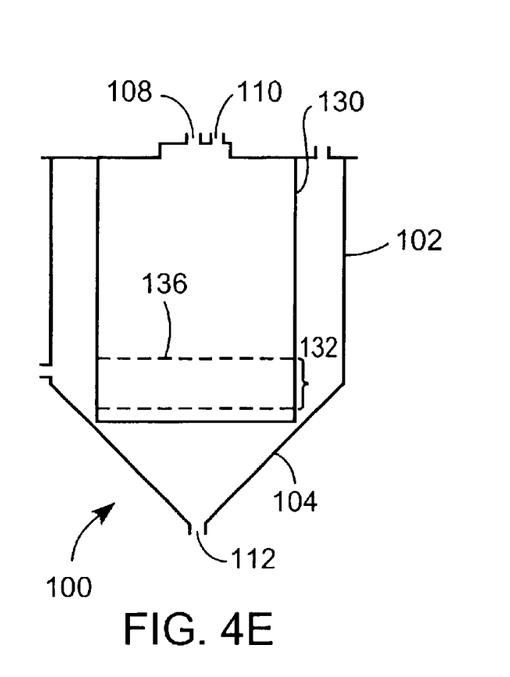
Figure 4F:
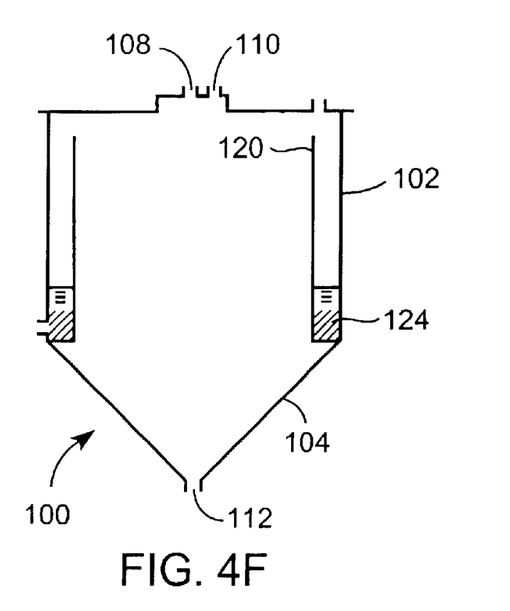

As shown in FIG. 4E, the leaching zone 136 at the bottom of the high solids zone 134 comprises a permeable section 132 of the inner wall 130, or a screen, wherein the openings constitute approximately 60% of the total perimeter area of the leaching zone.

The outer hydraulic reservoir zone 124 is defined between the intermediate wall 120 and the outer vessel wall 120, and can be typically provided with a 30,000–40,000 gallon capacity for a vessel of the size represented by the example shown in FIGS. 4A–4F. Fluids decant over a weir 121 formed by the top edge of the intermediate wall 120 as a function of the hydraulic head developed within the high solids zone 134 on the inside of inner wall 130. A portion of the fluids collected in the hydraulic reservoir 124 can be recycled through line 125 to be reintroduced through inlet 108 to the top of the high solids zone 134. A heat exchanger (such as 127 in FIGS. 2 and 3) can also be provided in the recycle line 125 if desired to maintain the temperatures within the vessel in a particular range optimal for the growth of the contained microorganisms. In the essentially closed loop of the embodiment shown in FIG. 3, a portion 125' of the fluids being recycled through recycle line 125 can be combined with pressate 115, treated biomass 20 and cellulose fiber fines 64 to obtain a mixture with the proper percentage of fluids for further density separation in a liquid cyclone 50 before being reintroduced into the hybrid digester 100. The attached growth media zone 122 retains the methane producing organisms such that removal of a sufficient amount of fluids to obtain the necessary dilution for operation of the liquid cyclone 50 is possible without interfering with the efficient processing of the fluids within the hybrid digester 100 and conversion to biogas.

The principles, preferred embodiments and modes of operation of the present invention have been described in the foregoing specification. However, the invention which is intended to be protected is not to be construed as limited to the particular embodiments or examples disclosed. Further, the embodiments and examples described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A method of treating waste material, including organic and inorganic materials with the organic materials including starches, cellulose and other carbohydrates, the method comprising:
   subjecting the waste material to increased temperature, pressure and moisture within an apparatus by introducing steam into the apparatus;
   increasing the temperature and pressure within the apparatus by an effective amount to cause the steam to reach a saturated state within the apparatus;
   rapidly reducing the pressure within the apparatus to reach a pressure less than atmospheric and to cause the steam to become superheated;
   removing the material from the apparatus and passing the material through a screen to separate the material by size; and
   diluting at least a first portion of the material with water while agitating the resulting diluted mixture a sufficient amount and at an effective temperature to cause cellulose fibers that became twisted and tangled during processing within the apparatus to relax and straighten out or untangle.

2. The method according to claim 1, wherein the first portion of the material is the portion that has passed through a 0.5 inch screen.

3. The method according to claim 1, wherein the dilution step results in a mixture that is approximately 4% solids and 96% fluids.

4. The method according to claim 1, further including separating the diluted mixture by density in a liquid cyclone.

5. The method according to claim 1, further including separating the diluted mixture by size using a screen.

6. The method according to claim 1, further including adding at least a portion of the diluted and separated mixture to an anaerobic digester wherein the portion of the mixture is converted to one or more of a biogas suitable for use as fuel, and a residual sludge suitable for use as compost, soil amendment and solid fuel.

7. The method according to claim 1, wherein the effective temperature of the diluted mixture is approximately 130° F.

8. The method according to claim 1, further including separating the diluted mixture by density, separating the diluted mixture by size, thickening the diluted mixture by squeezing or other processes to reach approximately 50% solids and 50% fluids consistency, and adding the 50% solids and 50% fluids mixture to an anaerobic digester.

9. The method according to claim 8, further including separating the fluids from the solids within the anaerobic digester and producing a biogas comprising $CO_2$ and methane as well as residual material suitable of use as a solid fuel and/or compost by the biological actions of microorganisms selected from a group of microorganisms consisting of acid forming organisms, hydrogen reducing organisms and methane forming organisms.

10. The method according to claim 9, wherein the fluids are leached out from the solids contained within a central zone of the anaerobic digester, and the fluids enter an attached growth media zone surrounding the central zone.

11. The method according to claim 10, wherein fluids within the attached growth media zone are decanted over a weir formed by a top edge of an intermediate wall defining the outer periphery of the attached growth media zone and into a hydraulic reservoir defined between the intermediate wall and an outer wall of the anaerobic digester.

12. A method of treating waste material, comprising:
   subjecting the waste material to increased temperature, pressure and mechanical shearing action in an apparatus to produce a biomass having at least one characteristic selected from a group of characteristics consisting of a higher freeness or greater ability to rapidly drain water than conventional recyclable ground wood pulp, finer particle sizes than those achieved by conventional hydro-pulping of waste material for the same amount of energy consumed, aseptic properties, the majority of organic material in the biomass being solubilized and increased biodegradability of cellulose fibers in comparison to cellulose fibers that have not been subjected to similar processing; and
   subjecting the biomass to a gravity separation process wherein components of the biomass are separated by density.

13. The method of claim 12, further including diluting the biomass with process water and subjecting the resulting diluted mixture to a pulping or mixing action.

14. The method of claim 13, wherein the biomass is diluted to approximately 4% solids content.

15. The method of claim 14, wherein the diluted mixture is maintained at approximately 130° F. for approximately 30 minutes.

16. The method of claim 15, further including thickening the diluted mixture to approximately 50% solids and 50% liquids consistency.

17. The method of claim 16, further including adding the thickened mixture to an anaerobic digester.

18. The method of claim 17, further including separating fluids from solids within the anaerobic digester and producing a biogas comprising $CO_2$ and methane by the biological actions of methane-producing organisms, and a residual material suitable as a solid fuel and/or compost.

19. The method of claim 18, wherein the fluids are leached out from the solids contained within a central zone of the anaerobic digester, and enter an attached growth media zone surrounding the central zone, wherein the methane-producing organisms remain attached to media contained within the attached growth media zone.

20. The method of claim 19, wherein fluids within the attached growth media zone are decanted over a weir formed by a top edge of an intermediate wall defining the outer periphery of the attached growth media zone and into a hydraulic reservoir defined between the intermediate wall and an outer wall of the anaerobic digester.

21. The method of claim 12, further including adding a portion of the biomass separated during the gravity separation process to a hybrid anaerobic digester having separate zones for biological processing of a solids portion of the biomass and a fluids portion of the biomass.

22. The method of claim 21, wherein the fluids portion of the biomass is leached out from the solids portion of the biomass contained within a central zone of the hybrid anaerobic digester, and the fluids portion enters an attached growth media zone surrounding the central zone, wherein methane-producing microorganisms remain attached to media contained within the attached growth media zone.

23. The method of claim 22, wherein fluids within the attached growth media zone are decanted over a weir formed by a top edge of an intermediate wall defining the outer periphery of the attached growth media zone and into a hydraulic reservoir defined between the intermediate wall and an outer wall of the anaerobic digester.

24. The method of claim 23, wherein fluids from the hydraulic reservoir are added to biomass from the apparatus and the mixture is subjected to the gravity separation process before being added to the hybrid anaerobic digester.

25. A hybrid anaerobic digester, comprising:

a vessel having an outer wall;

an intermediate wall spaced inwardly from said outer wall and a hydraulic reservoir defined between said intermediate wall and said outer wall;

an inner wall spaced inwardly from said intermediate wall and an attached growth media zone containing growth media defined between said inner wall and said intermediate wall; and a lower portion of said inner wall being permeable to provide fluid communication between an inner zone defined within said inner wall and said attached growth media zone.

26. The hybrid anaerobic digester according to claim 25, wherein bars are positioned across a lower portion of said inner zone, said bars adapted to break up material dropping past said bars from said inner zone.

27. The hybrid anaerobic digester according to claim 25, wherein said vessel tapers in at its lower end to form a conical compaction zone below said inner zone.

28. The hybrid anaerobic digester according to claim 25, wherein an outlet is provided through said outer wall in fluid communication with said hydraulic reservoir and connecting through a recycle line to the top of the inner zone.

29. The hybrid anaerobic digester according to claim 28, wherein temperature is controlled in said recycle line to maintain temperature within said vessel within the desired range.

30. The hybrid anaerobic digester according to claim 25, wherein a head space for collection of gases produced within said vessel is defined at the top of said vessel at least above the inner zone.

* * * * *